US005637099A

United States Patent [19]
Durdin et al.

[11] Patent Number: 5,637,099
[45] Date of Patent: Jun. 10, 1997

[54] NEEDLE HANDLING APPARATUS AND METHODS

[76] Inventors: Daniel J. Durdin, 11262 N. Eagle Lake Blvd., Maple Grove, Minn. 55369; Mark D. Anderson, 23155 E. Marin Lake Dr., Stacy, Minn. 55079; William D. Saville, 873 97th St., N.W., Monticello, Minn. 55362; Nancy L. Thompson, 1212 Reston Ave., Herndon, Va. 22070

[21] Appl. No.: 257,739

[22] Filed: Jun. 9, 1994

[51] Int. Cl.⁶ ............................ A61M 5/32; A61M 5/00
[52] U.S. Cl. ................................. 604/192; 604/110
[58] Field of Search ........................ 604/110, 192, 604/263, 187; 128/919; 206/366

[56] References Cited

U.S. PATENT DOCUMENTS

| | | |
|---|---|---|
| 3,451,540 | 6/1969 | Kulischenko . |
| 4,351,434 | 9/1982 | Elisha . |
| 4,410,086 | 10/1983 | Simpson . |
| 4,488,643 | 12/1984 | Pepper . |
| 4,520,926 | 6/1985 | Nelson ............... 206/366 |
| 4,576,211 | 3/1986 | Valentini et al. . |
| 4,600,112 | 7/1986 | Shillington et al. ......... 206/366 |
| 4,675,006 | 6/1987 | Hrushesky . |
| 4,722,472 | 2/1988 | Bruno . |
| 4,755,170 | 7/1988 | Golden . |
| 4,801,013 | 1/1989 | Bruno . |
| 4,840,185 | 6/1989 | Hernandez . |
| 4,846,808 | 7/1989 | Haber . |
| 4,862,573 | 9/1989 | Kelson et al. . |
| 4,895,346 | 1/1990 | Steigerwald . |
| 4,927,018 | 5/1990 | Yang et al. . |
| 4,927,415 | 5/1990 | Brodsky ............... 604/164 |
| 4,929,235 | 5/1990 | Merry et al. . |
| 4,932,946 | 6/1990 | Shields . |
| 4,956,907 | 9/1990 | Bruno . |
| 4,986,811 | 1/1991 | Thead et al. . |
| 4,986,817 | 1/1991 | Code . |
| 4,997,422 | 3/1991 | Chow et al. . |
| 5,078,694 | 1/1992 | Wallace . |
| 5,104,388 | 4/1992 | Quackenbush . |
| 5,143,414 | 9/1992 | Rosellini . |
| 5,169,393 | 12/1992 | Moorehead et al. . |
| 5,171,229 | 12/1992 | McNeil et al. . |
| 5,176,655 | 1/1993 | McCormick et al. . |
| 5,209,733 | 5/1993 | Lever et al. ............... 604/110 |
| 5,212,362 | 5/1993 | Burden et al. . |
| 5,259,501 | 11/1993 | Withers et al. . |
| 5,267,975 | 12/1993 | Brodsky ............... 604/198 |
| 5,305,766 | 4/1994 | Hahn . |
| 5,312,346 | 5/1994 | Han . |

*Primary Examiner*—Robert A. Hafer
*Assistant Examiner*—Benjamin K. Koo
*Attorney, Agent, or Firm*—Merchant, Gould, Smith, Edell, Welter & Schmidt

[57] ABSTRACT

An apparatus for safely handling a needle while removing the needle from a substrate such as an implanted access device having a resealable septum. The apparatus has a distal end and a proximal end and comprises a body, a cap member, and a basin-shaped member. The body defines interior boundaries and the cap member has an opening therein. The cap member is connected to and is distal to the body. The basin-shaped member defines a self-closing passageway and has a rim connected to the body. The rim of the basin-shaped member is disposed within the interior of the body intermediate the cap member and the proximal end of the apparatus. The basin-shaped member has an apical end facing the distal end of the apparatus. The cap member includes two resilient flaps, offset from one another. In one arrangement, the cap member and the body snap together to trap the basin-shaped member. In another arrangement, the apparatus is made of two identical halves joined together. An adapter is provided to facilitate use of the apparatus with small ports.

36 Claims, 10 Drawing Sheets

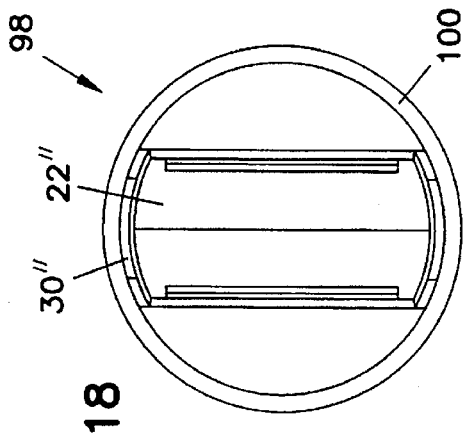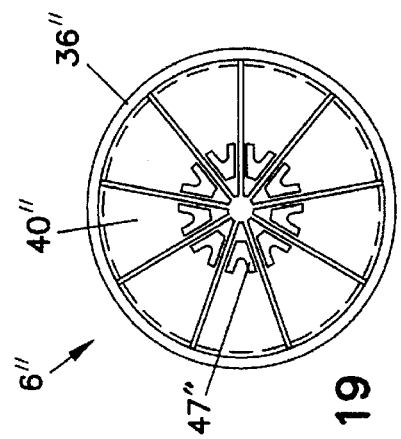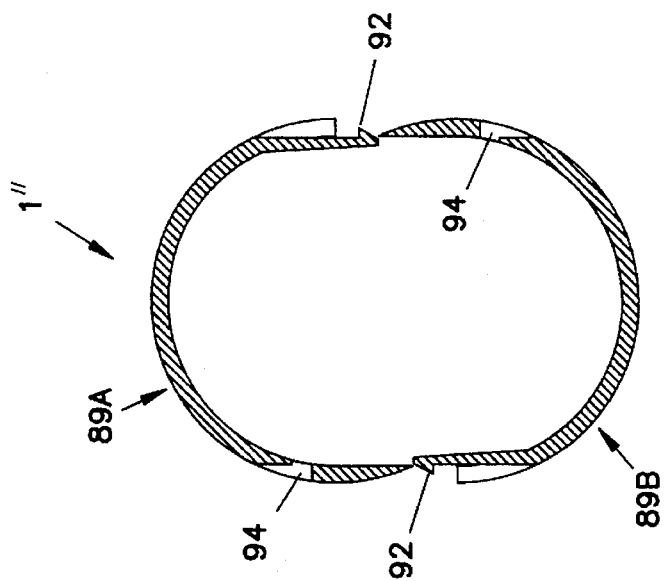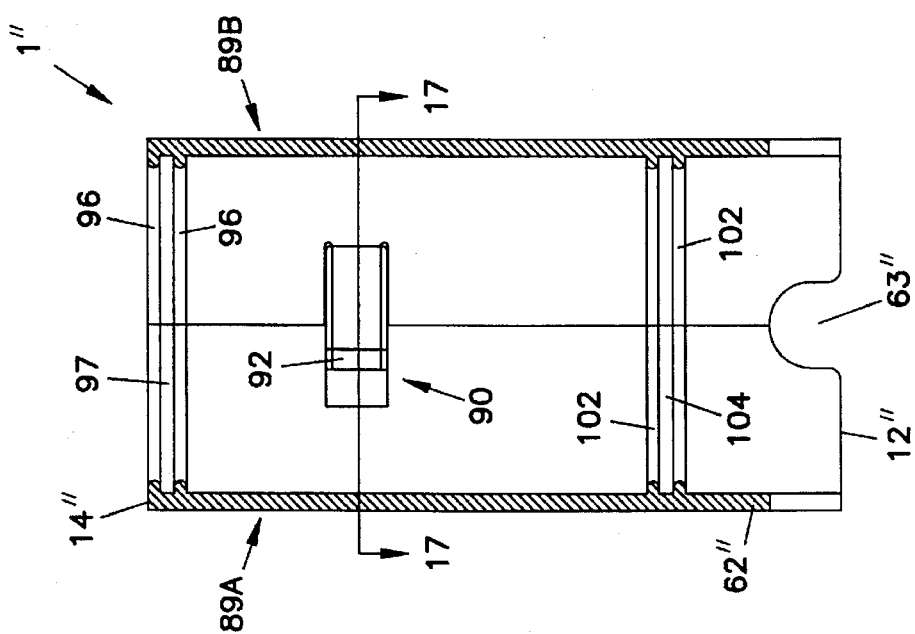

NEEDLE HANDLING APPARATUS AND METHODS

FIELD OF THE INVENTION

This invention relates to apparatus and methods for safely removing a medical needle inserted into an implanted access device under the skin of a patient and the disposing of the medical needle.

BACKGROUND OF THE INVENTION

Delivery of fluids, for example, saline solution or medicine, into a body cavity or a vessel, such as a vein or an artery, of a patient is sometimes necessary for therapeutic and health maintenance reasons. In some cases, fluids need to be delivered to the patient periodically or continuously. In such an instance, repeated injection through the skin into a vessel of the patient is undesirable because of the trauma caused by such repeated injection to the vessel. An access device is often used, which includes a portal and a small, flexible, hollow tubing (i.e., a catheter) extending from the portal and into a vessel where it remains for a prolonged period of time such that fluids may be repeatedly or continuously infused through the catheter into the vessel. Other parts of the body can be accessed other than a vein or artery with the implanted access device. Removal of body fluids may also be handled through the access device.

The portal of the access device is implanted under the skin and has a septum through which a medical needle can be inserted to provide fluid communication between the medical needle and the vein, artery, or other body location. To prevent fluid leakage through the septum, generally the septum is self-sealing, i.e., the septum is composed of a resilient material that presses on the shaft of the medical needle that is inserted in the septum. The pressure by the septum on the medical needle results in a force resisting the withdrawal of the needle from the septum, thereby making it necessary for a health professional to hold the access device down against the patient as the medical needle is withdrawn therefrom. If the health professional attempts to hold the portal (i.e., the structure defining the chamber in conjunction with the septum of the access device) down with his or her fingers, withdrawing the medical needle from the septum may cause the medical needle to accidentally prick or strike the health professional's finger.

A medical needle, such as a hypodermic needle or a butterfly needle, that has been exposed to a body fluid of a patient with an infectious disease, can pose a health risk to health professionals if the needle is not properly removed and disposed of using an apparatus suitable for safely handling such medical needles. For example, a medical needle that has been used on a patient with hepatitis B or HIV (or AIDS) virus, if allowed to accidentally prick the skin of a health professional, may transmit the disease to that health professional.

There is a need in the art for apparatus and methods for removing and isolating a medical needle that has been inserted into a septum of an implanted access device.

SUMMARY OF THE INVENTION

The present invention meets a need for an apparatus for removing and isolating a medical needle wherein the apparatus has a lower self-closing passageway wherein a needle-removal device, such as a hemostat, forceps, locking tweezers, and the like, can be used to draw a medical needle through the passageway to isolate the medical needle in the apparatus such that the medical needle cannot independently extend outside the apparatus to accidentally prick a health professional. Preferably, an upper self-closing passageway is provided to selectively allow passage of the needle-removal device but not the medical needle.

The present invention provides an apparatus for safely handling a needle (i.e., medical needle), for example, in removing the medical needle from a substrate, such as the skin of patient or an implanted access device. The apparatus has a distal end and a proximal end and comprises a body, a cap member defining an opening therein and connected to the body to define an interior, and a lower yieldable partition member, preferably a basin-shaped member, connected to the body wherein the cap member is distal to the body. The basin-shaped member is comprised of one or more yieldable flaps or fingers. The basin-shaped member may have any of a plurality of configurations, including flat, V-shaped, dome-shaped, or conical-shaped. As used herein, the term "proximal" refers to a direction towards the substrate and the term "distal" refers to a direction away from the substrate. The basin-shaped member (lower yieldable partition member) defines a self-closing passageway and preferably has a rim disposed within the interior of the body intermediate the cap member and the proximal end of the apparatus. The apical end of the basin-shaped member faces the distal end of the apparatus. The term "self-closing" refers to the ability of the passageway to return to its normally closed configuration after a force that deforms the passageway is removed. The normally closed configuration prevents a medical needle from independently extending therethrough.

Preferably, a snap arrangement is provided to mount the body to the cap member wherein the lower yieldable partition member is held between portions of the body and the cap member.

The present invention also provides an apparatus for safely handling a needle wherein the apparatus has a distal end and a proximal end and comprises a body, a cap member defining an opening therein, and an upper yieldable partition member connected to the cap member. The cap member is connected to and disposed distally to the body to define an interior. The upper yieldable partition member preferably has two generally rectangular flaps yieldably connected to the cap member. The generally rectangular flaps preferably extend obliquely toward each other and toward the interior. Each flap terminates at a free edge, and the free edges of the flaps are proximate to and preferably offset from each other in the direction toward the proximal end. The upper yieldable partition member defines a self-closing passageway which can be disposed within the interior intermediate the distal end and the proximal end of the apparatus, or preferably, proximate the distal end. The offset configuration is optional but it may lead to ease of manufacturing in the case of molded plastics where the flaps need to be appropriately positioned to prevent the passage of the medical needle.

The apparatus for safely handling a medical needle of the present invention is particularly adapted for use in removing a medical needle that has been inserted into an implanted access device for the periodical or continuous infusing or withdrawal of a fluid through the medical needle. The apparatus can be used to completely isolate the medical needle from the health professional. For example, a hemostat can be used to remove the medical needle with the apparatus disposed between the medical needle and the health professional. The health professional can remove the medical needle from the implanted access device and deposit the medical needle in a cavity in the apparatus, which prevents the medical needle from independently and accidentally protruding or extending therethrough, all the while keeping at least part of the apparatus between the medical needle and the health professional. In addition, the lower yieldable partition member having the self-closing passageway is preferably non-planar, having an apical end facing the interior of the cavity wherein the medical needle is disposed. Thus, the medical needle is kept from the open ends of the apparatus and the risk of accidentally exposing the health professional to the contaminated medical needle is further reduced. Moreover, the medical needle cannot easily pass back through the lower non-planar self-closing passageway due to its apical configuration and orientation relative to the medical-needle-receiving cavity. Such a self-closing passageway is a "one-way passageway" because it is relatively easy to draw a medical needle into the interior of the cavity through the self-closing passageway but more difficult to move a medical needle in the other direction. The upper yieldable partition member allows passage of the medical tool to grasp the needle during removal from the access device, while preventing passage of medical needle.

In an embodiment of the apparatus of the present invention, the basin-shaped member facilities the assembly of the apparatus because the basin-shaped member is self-centering when placed on the proximal end of the cap member with the apical end facing the cap member. In other embodiments, the apparatus is composed of identical halves. This simplifies the tooling cost and inventory cost for parts during the manufacturing process. The apparatus of the present invention can be applied to implanted access devices of various sizes because an adaptor according to the present invention can be used to adapt the apparatus for application on a smaller implanted access device.

BRIEF DESCRIPTION OF THE DRAWINGS

The preferred embodiments of the present invention are shown in the following drawings, wherein like reference numerals represent like corresponding parts in the several views:

FIG. 16 is a cross-sectional view of a third preferred embodiment of the apparatus of the present invention, with the basin-shaped member and the cover member removed for clarity;

FIG. 17 is a cross-sectional view of the two halves along the line 17—17 of FIG. 16 with portions removed for clarity;

FIG. 18 is a top view of a cover member for use with the structure of FIG. 16;

FIG. 19 is a basin-shaped member for use with the structure of FIG. 16;

DETAILED DESCRIPTION OF THE PREFERRED EMBODIMENTS

The present invention provides an apparatus and method for safely handling medical needles engaged with the septum of an access device implanted under the skin of a patient. Two spaced apart yieldable partition members define a cavity for safely containing a medical needle. A needle-removal device passes through both partition members to grasp the medical needle and withdraw the medical needle past the lower partition member. The lower partition member is self-closing to close the lower end of the apparatus. The needle-removal device releases the medical needle in the cavity of the apparatus, and is withdrawn from the upper partition member. The upper partition member is self-closing to close the upper partition member. While the terms "upper" and "lower" are used herein, it is to be appreciated that such orientation relative to the vertical occurs in one preferred mode of operation. The apparatus of the present invention is useable at any angle to the vertical, including perpendicular.

Figure 1:
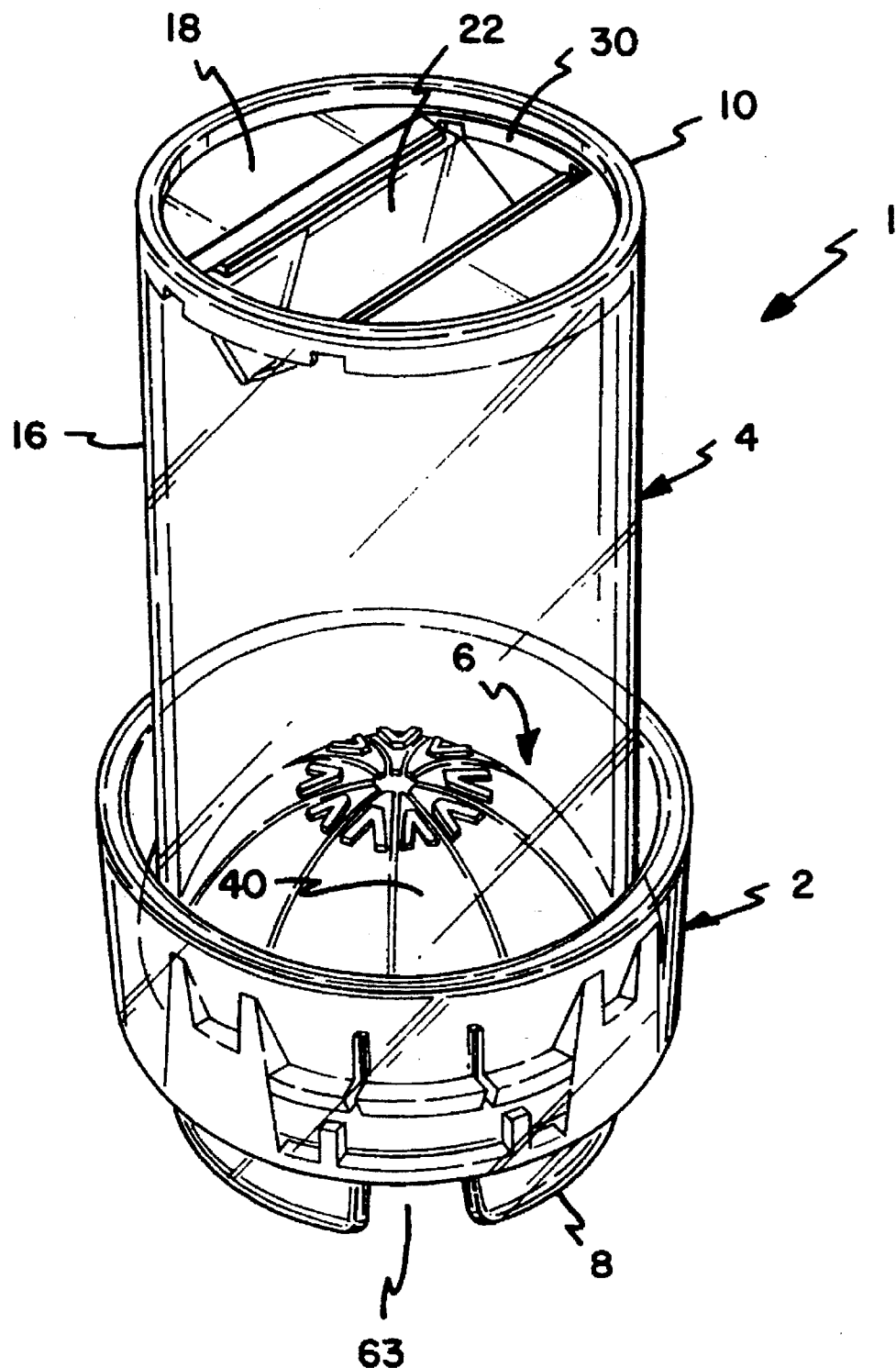
FIG. 1 is an isometric view of a first preferred embodiment of an apparatus of the present invention.
Figure 2:
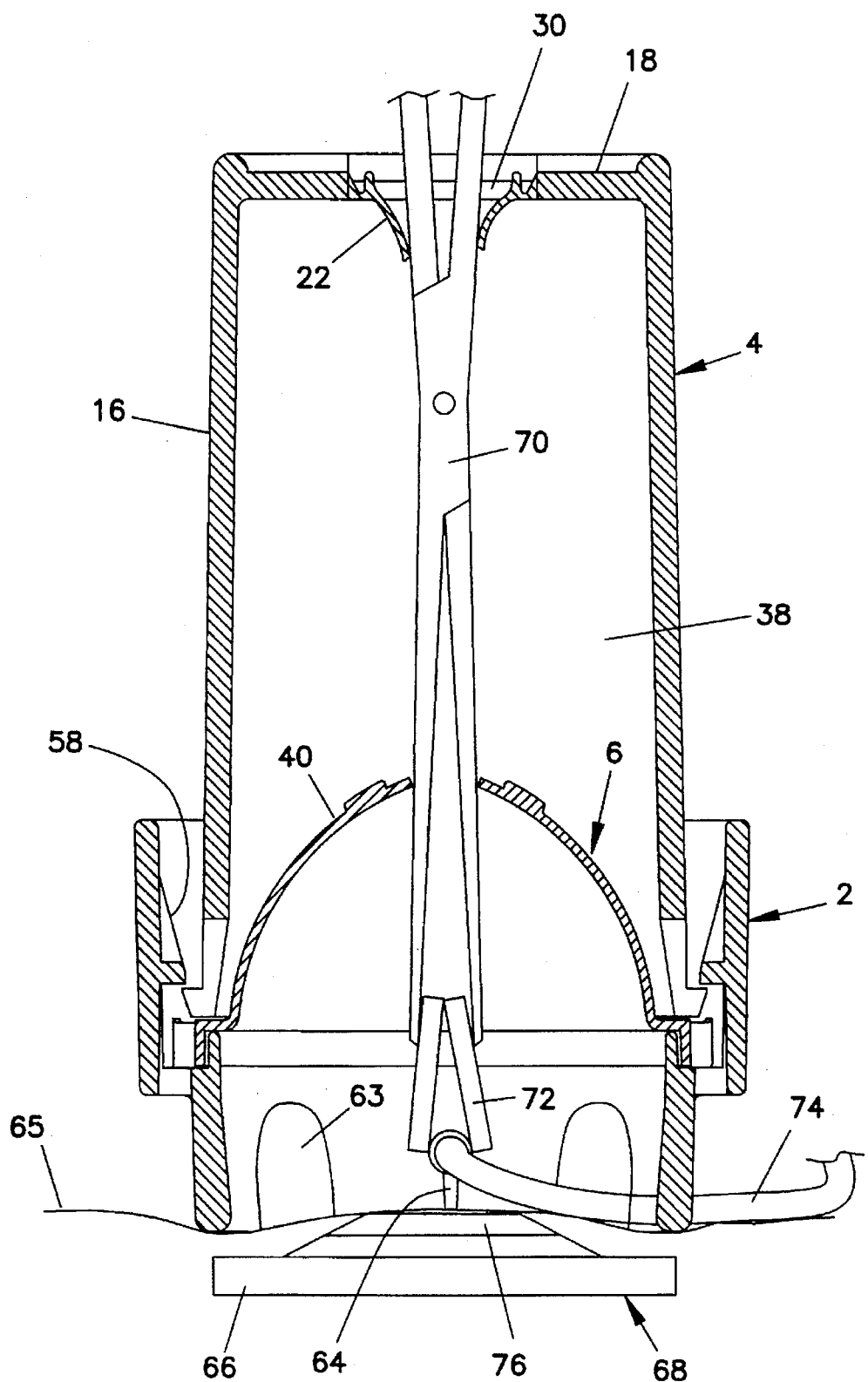
FIG. 2 is a partial cross-sectional view of the embodiment of FIG. 1 deployed over an implanted access device.
Figure 3:
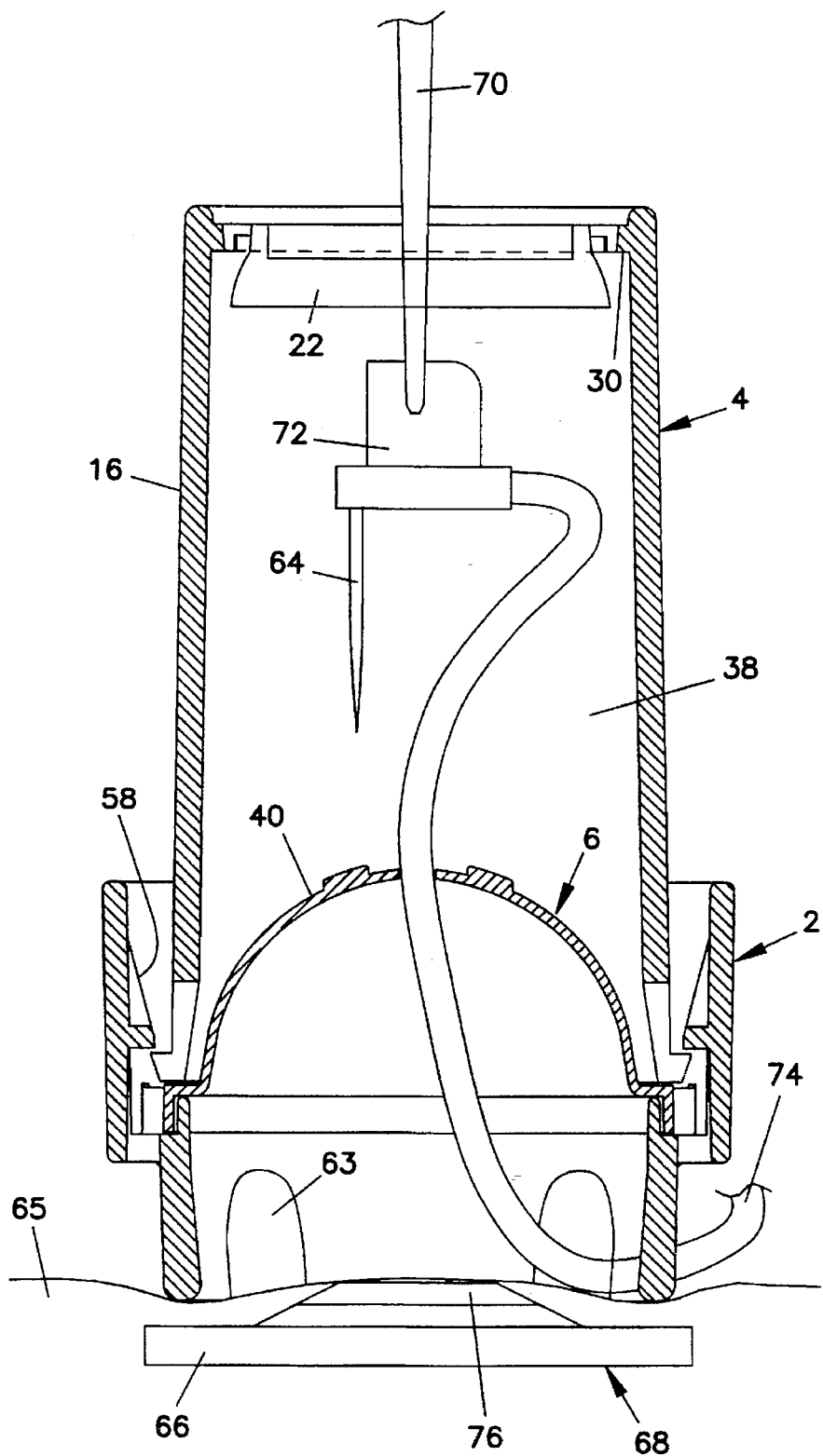
FIG. 3 is a partial cross-sectional view at a right angle to that of FIG. 2, showing the removal of a medical needle from the implanted access device.
Figure 4:
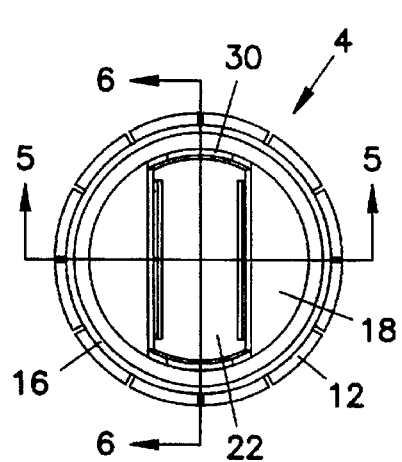
FIG. 4 is a top view of a cap member of the embodiment of FIG. 1.
Figure 6:
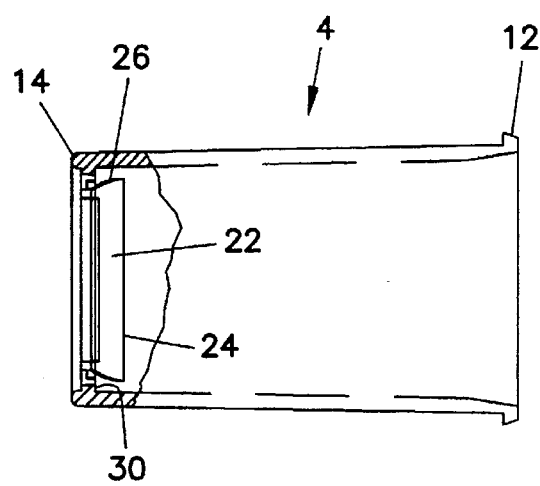
FIG. 6 is a partial cross-sectional view along the line 6—6 of FIG. 4.
Figure 5:
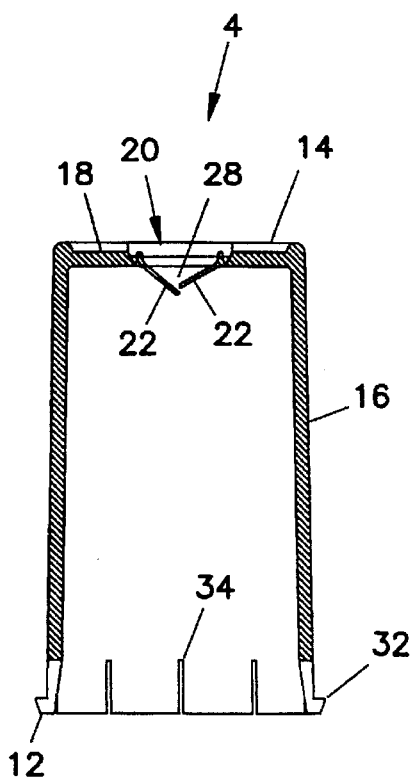
FIG. 5 is a cross-sectional view along the line 5—5 of FIG. 4.
Figure 7:
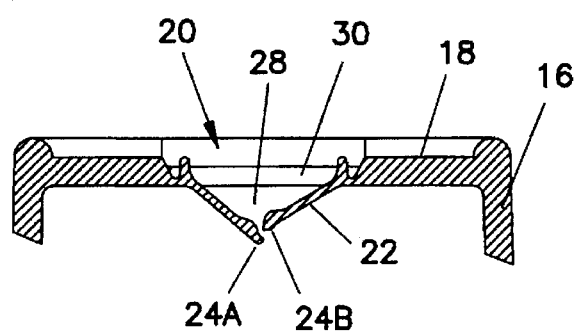
FIG. 7 is an enlarged cross-sectional view showing details along the line 5—5 of FIG. 4.

A first preferred embodiment of this invention is shown in FIGS. 1-13. Referring now to FIGS. 1-3, the apparatus 1 has a body construction with an accessible interior for containing a medical needle during use. Specifically, apparatus 1 includes a body 2, a cap member 4, and a basin-shaped or cup-shaped member 6. The apparatus has a proximal end 8 and a distal end 10.

Referring to FIGS. 4-7, the cap member 4 has a proximal end 12 and a distal end 14 and is disposed generally distal to the body 2. The cap member 4 is generally cylindrical and has a peripheral wall 16 and a distal end wall 18 defining the interior boundaries. An opening 20 is preferably located on the distal end wall 18 proximate the distal end 14 of the cap member 4. The opening 20 is configured to permit a needle-removal device to pass therethrough, such as a hemostat or another gripping device. The opening 20 can simply be edges defining an opening to permit the free passage of the needle-removal device, or it can include a structure that guards the opening to permit a needle-removal device to pass therethrough but prevent the medical needle to independently (i.e. without the deliberate manipulation by an operator) extend or exit therethrough. This structure forms an upper (or distal) yieldable partition member.

A preferred structure for guarding the opening 20 to render it self-closable includes a flap 22 integrally and yieldably connected to the rest of the cap member 4 such that a needle-removal device can be forcefully pressed against the flap 22 to pass thereby. The flap 22 is generally rectangular and resiliently flexible (or yieldable to pressure) to provide a self-closing passageway into the interior of the cap member. Upon withdrawal of the needle-removal device, the resilient nature of the flap 22 returns the flap to its normally closed position. The flap 22 can extend toward the interior of cap member 4 to facilitate the selective passage configuration with respect to the medical needle and the needle-removal device. A flat flap 22 extending perpendicularly to the axis of the cap member may be utilized as a self-closing passageway.

Preferably, there are two flaps 22 extending toward each other, preferably obliquely and toward the interior of the cap member 4, each terminating at a free edge 24 opposite from where the flap is connected to the end wall 18. Each flap 22 has two side edges 26 joined to the free edge 24, defining the flap. The free edges 24 of the two flaps 22 are proximate to each other and are substantially parallel. Preferably, the flaps 22 are slightly off-set (e.g., about 0.04 in. to 0.08 in.) in the direction toward the proximal end 12 such that the free edge 24 of one flap is at a longitudinal location different from that of the free edge of the other flap. These two free edges 24A,24B are aligned along a plane extending through the proximal end 12 and the distal end 14 so that viewing from the distal end of the cap member, the free edges 24A,24B substantially coincide (see for example, FIG. 4). In this way, the size of the gap between the free edges from a vertical (or end view) perspective (e.g., about 0.020 in. to 0.025 in.) can be made smaller than the diameter of a shaft of a medical needle (e.g., about 0.028 in. for 22 gauge needle), even though the actual gap is wider when viewed at an angle to the vertical. Because of the limited space between the flaps 22 and the side walls of the cap member 4, a medical needle will not extend through the gap from the interior of the cap member 4. The offset allows ease of manufacturing to provide the small gap in the longitudinal direction, yet not requiring tight tolerances or difficult-to-configure parts molds to achieve the small gap.

The length of the free edges 24 of the flaps are preferably of a dimension such that the side edges 26 are proximate the cylindrical wall 16 of the cap member so as to reduce the risk of a medical needle extending through a gap 28 defined by the side edges 26 of the flaps and a side edge of the opening. To further reduce this risk, the opening 20 can further include lips 30 extending from the wall 16 of the cap member 4 radially inward proximate the end wall 16. The lips 30 are oriented generally perpendicular to the free edges 24 of the flaps 22 to prevent a medical needle from sliding along the wall of the cap member to extend into a space (or gap) 28 distal to the flaps and proximate the side edges 24 thereof.

The cap member 4 is connected, preferably rotatably engaged, to the body 2. As used herein, the term "connected" when applied to the relation between the cap member 4, the basin-shaped member 6 having the self-closing passage, and/or the body 2 includes a rigid connection between the parts, whether integrally formed, or intimate engagement in which one part can move, such as by rotation, in relation to the other part. The rotation of the cap member 4 relative to the body 2 facilitates the positioning of a needle-removal device, such as a hemostat or locking tweezers for passing through the cap member. The cap member 4 can be connected to the body 2 by arrangements of corresponding matingly engageable fastening structures effective to fasten the cap member 4 and the body 2 without the need of an externally applied securing device such as adhesive, tape, clamp, screw, nut with bolt, and the like. The corresponding matingly engageable fastening structures of the cap member 4 and the body 2 can be of a configuration such that they can be fitted together with a snap-fit. Preferably, the matingly engageable fastening structures of the snap-fitted apparatus resists the separation of the cap member 4 from the body 2 but permits relative rotation thereof. Located on the proximal end 12 and disposed on the exterior surface of the cap member 4 is a generally annular lip 32 for such a mating engagement with wedge-shaped members (shown as 58 in FIG. 12) of the body 2. Furthermore, preferably, slits 34 are provided on the portion of the cap member at its proximal end to increase the flexibility thereof. The annular lip 32 disposed on the proximal, exterior surface of the cap member 4 preferably is beveled to have a larger diameter on its distal edge than its proximal edge to facilitate slipping the annular lip past the wedge-shaped member for snap-fit engagement.

Figure 8:
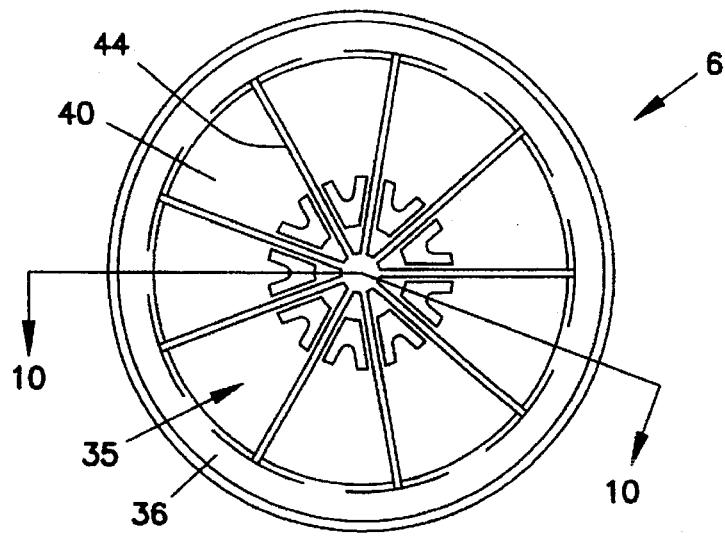
FIG. 8 is a top view of the basin-shaped member of FIG. 1.
Figure 9:
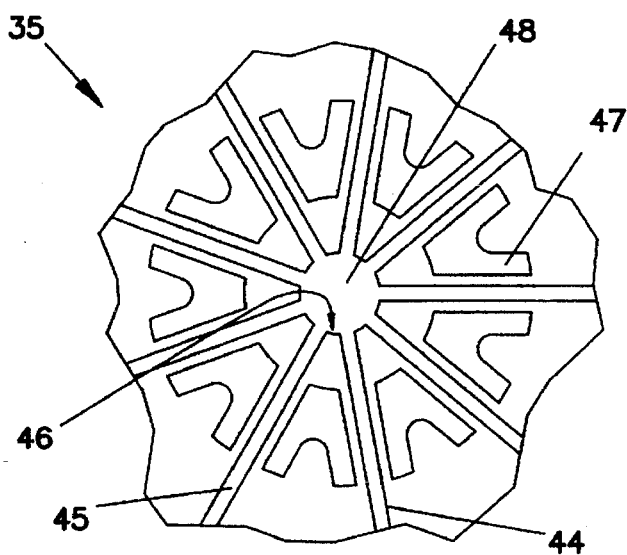
FIG. 9 is an enlarged view showing details of a portion of FIG. 8.
Figure 10:
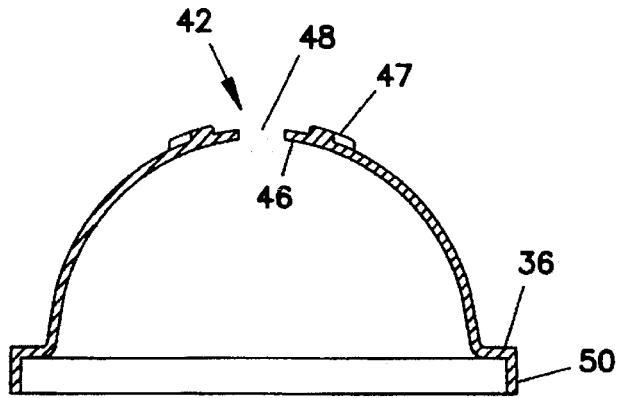
FIG. 10 is a cross-sectional view along the line 10—10 of FIG. 8.

Referring to FIGS. 8–10, the basin-shaped member 6 defines a self-closing passageway 35 and has an annular rim 36. The basin-shaped member 6 forms a lower (or proximal) yieldable partition member with self-closing capability. Preferably, although not required, the lower yieldable partition member is one-directional with respect to the passage of a medical needle during use, meaning that entry of the medical needle is easier than exiting. Most preferably, the one-directional feature makes it difficult or impossible for the medical needle to pass in the opposite direction. A flat configuration for member 6 is possible where member 6 is still self-closing. In that case, additional structure may be necessary to make the flat member one-directional, if desired. The basin-shaped member 6, in cooperation with the cap member 4, defines a cavity (shown as 38 in FIGS. 2–3). As shown in FIGS. 8–10, the basin-shaped member has a plurality of yieldable (or resiliently flexible), generally umbrella-section-shaped members (or fingers) 40 extending therefrom to cumulate at an apical end 42 to have a dome-shaped appearance. Each finger 40 further has side edges 44 extending inwardly and toward the distal end 42 of the apparatus to cumulate at the apical end, which faces the distal end 10 of the apparatus. The side edges of two adjacent fingers define a slot 45 therebetween. Preferably, although not required, the side edges 44 and tips 46 of neighboring fingers do not touch each other so as to permit free movement of the fingers. Because the fingers 40 are curved, the tips 46 of the fingers are generally aligned and do not form sharp angles with each other when viewed from the side. In this way, the tips 46 of the fingers define a generally circular opening 48 (having a diameter of, for example, 0.11 in.) through which the tip of the needle-removal device can extend to spread apart the tips 46 of the fingers. As can be seen in FIGS. 2 and 3, the fingers 40 will yield to permit a needle-removal device to pass therethrough to grasp a medical needle and permit the medical needle to be pulled by the needle-removal device into the cavity 38 distal to the fingers in the apparatus. However, the fingers are proximate to each other so as to form a one-way partition through which a medical needle can be drawn. Such a one-way partition can prevent a medical needle from independently passing therethrough in the opposite direction, for example, by rotational or vibrational movement of the apparatus. The non-planar configuration provides for an easier passage of a medical needle toward the apical end 42 from below the basin-shaped member 6 as shown in FIGS. 2 and 3, than in an opposite direction. It is to be appreciated that other non-planar shapes producing a one-way valve are possible other than the curved configuration shown, including generally planar fingers defining a conical shape, for example. Also, it is to be appreciated that basin-shaped member 6 does not have to be generally symmetrical about the longitudinal axis of the apparatus 1. For example, basin-shaped member 6 can have a single flexible finger or flap, or two opposed fingers or flaps, such as shown in connection with cap member 4.

Preferably, the basin-shaped member 6 has an odd number of fingers 40 so that no two slits 45 between the fingers are aligned in a straight line. Because butterfly needles (i.e., medical needles equipped with butterfly wings for ease of handling) are often used for application with implanted access devices and the butterfly wings of a butterfly needle are generally aligned in a plane during use, such a finger configuration, by blocking the butterfly wings, greatly reduces the risk of a butterfly needle independently passing through the basin-shaped member 6.

Also provided on the fingers proximate the tips thereof are elevated elements 47, such as V-shape ridges, for strengthening the tips mechanically. These elevated elements provide an added longitudinal dimension proximate the tips of the fingers so that even if two adjacent fingers are slightly misaligned or offset, the risk of a medical needle in the cavity 38 distal to the fingers 40 independently extending proximally through the basin-shaped member 6 is reduced.

The rim 36 is disposed in the interior of the body 2 intermediate the cap member 4 and the proximal end 8 of the apparatus 1. The self-closing passageway 35 is generally disposed inside the cavity 38 in the interior of the cap member 4 intermediate the proximal end and distal end of the apparatus. The self-closing passageway 35 is also disposed generally in the interior of the body 2, although it is to be appreciated that the basin-shaped member 6 may have a longitudinal dimension large enough that the apical end 42 extends distally past the distal end 54 of the body. Preferably, the rim 36 has an annular skirt 50 extending proximally for rotationally engaging a distally-extending, annular lip (shown as 60 in FIG. 13) integrally connected to the wall of the body on its interior surface. This skirt 50 limits the lateral movement of the basin-shaped member 6 in relation to the body 2. The rotational engagement of the basin-shaped member 6 with the annular interior lip 60 of the body 2 permits the basin-shaped member to be rotated in relation to the body for facilitating the removal of a medical needle through the basin-shaped member. The proximal portions of the fingers 40 form an angle with the rim of the basin-shaped member. The inside diameter of the rim 36 of the basin-shaped member 6 is slightly smaller than the inside diameter of the proximal portion of the peripheral wall 16 of the cap member 4 and the annular skirt 50 has an outside diameter larger than the inside diameter of the same peripheral wall so that during assembly of the apparatus 1, the basin-shaped member 6 can be positioned on the cap member 4 easily due to the self-centering nature of the basin-shaped member. Because the center of gravity of the basin-shaped member 6 is intermediate the rim 36 and the apical end 42, as the basin-shaped member is laid on the proximal end 12 of the cap member 4 with the proximal end 12 facing upward, the gravitational force draws the fingers 40 of the basin-shaped member into the interior defined by the peripheral wall 16 of the cap member. In this way, the nonplanar nature of the basin-shaped member 6 significantly increases the ease of assembly of apparatus 1 before use.

Figure 11:
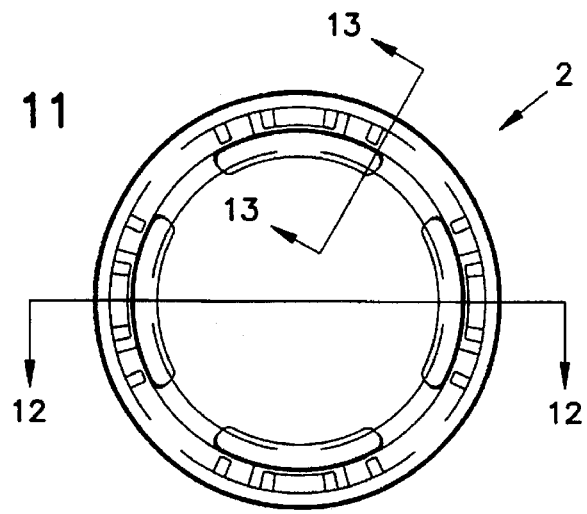
FIG. 11 is a top view of the body of the embodiment of FIG. 1.
Figure 12:
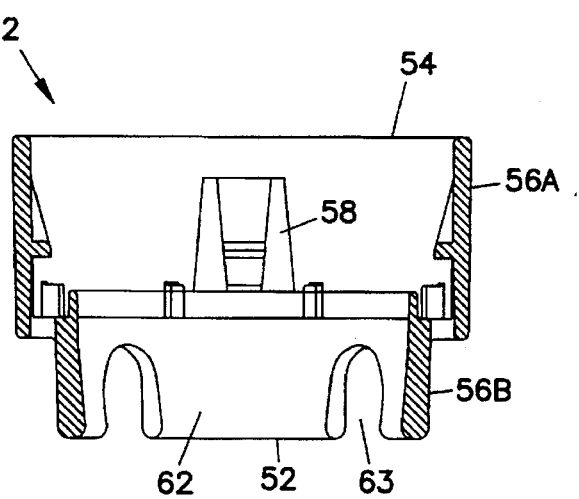
FIG. 12 is an enlarged cross-sectional view along the line 12—12 of FIG. 11.
Figure 13:
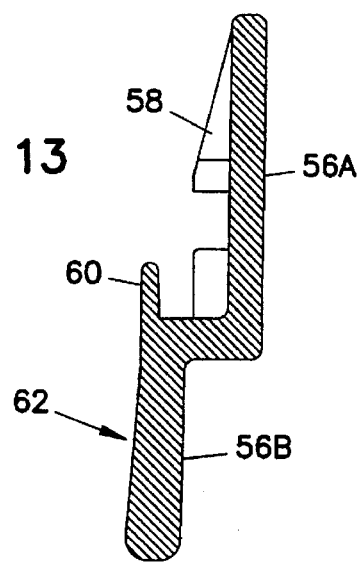
FIG. 13 is an enlarged cross-sectional view along the line 13—13 of FIG. 11.

Referring to FIGS. 11-13, the body 2 has a proximal end 52, a distal end 54, and walls 56A,56B defining interior boundaries thereof. On the inner surface of the wall 56A are disposed wedge-shaped members 58 which correspond to the proximal generally annular lip 32 of the cap member 4 for matingly engaging therewith to provide snap-fit fastening of the cap member 4 to the body 2 without externally applied fastening arrangements such as an adhesive, and the like. An interior annular lip 60 is provided proximal and more to the interior in relation to the wedge-shaped members 58. The annular lip 60 of the body 2 extends distally for engaging the inner surface of the annular skirt 50 of the basin-shaped member 6. In this manner, the annular lip 32 at the proximal end of the cap member 4 is disposed and rotationally confined between the wedge-shaped members 58 of the body and the annular interior lip 60 of the body. Furthermore, the rim 36 of the basin-shaped member 6 is rotationally held (or confined) between the generally annular lip 32 of the cap member 4 and the annular interior lip 60 of the body.

The body 2 further has a proximally extending portion 62 having dimensions slightly larger than the dimensions of the implanted access device so that a medical needle that has been inserted into the implanted access device is disposed in an interior space defined by the portion. Furthermore, provided on the proximal portion 62 proximate the proximal end of the apparatus are notches 63 through which a tubing 74 for infusing or withdrawal of liquid to the implanted access device can extend. The notches also allow for receipt of the catheter under the skin.

Referring to FIGS. 1-3 again, to remove a medical needle from an implanted access device implanted under the skin 65 of a patient, the apparatus 1 is pressed onto the skin above the portal 66 of the implanted access device 68. A needle-removal device 70, such as a hemostat or a pair of locking tweezers can be inserted through the opening defined by the flaps 22 and the lips 30 on the distal end of the cap member 4. The needle-removal device 70 flexes and slightly deforms the flaps 22 as it is inserted into the cavity 38 defined by the end wall and the peripheral wall of the cap member. Extending past the fingers 40 of the basin-shaped member, the needle-removal device 70 can be used to grasp the medical needle 64, for example, the butterfly wings 72 of a butterfly needle. As the needle-removal device 70 is manipulated to grasp and remove the medical needle from the septum 76 of the implanted access device, the fingers 40 of the basin-shaped member 6 are flexed to yield to the movement of the needle-removal device. The needle-removal device 70 can then be withdrawn, still grasping the medical needle, so that the medical needle is drawn past the apical end 42 of the basin-shaped member 6 (i.e., the tips of the fingers thereof) into the cavity 38 defined by the cap member and the basin-shaped member. The medical needle can then be released from the needle-removal device and the needle-removal device is withdrawn from the apparatus 1. In this manner, the medical needle is trapped in the cavity 38. The apparatus, with the medical needle confined therein, can then be properly disposed of without the risk of the medical needle independently extending outside the apparatus and posing a health risk to an operator. It is anticipated that the apparatus be disposable with the used medical needle inside.

Figure 15:
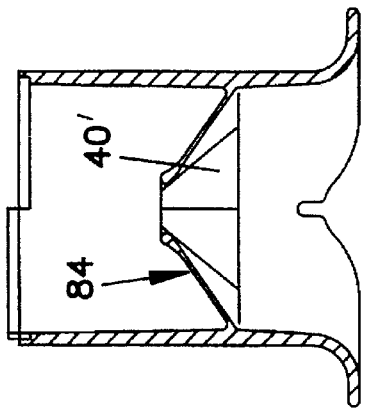
FIG. 15 is a cross-sectional view of one identical half of the embodiment of FIG. 14.
Figure 14:
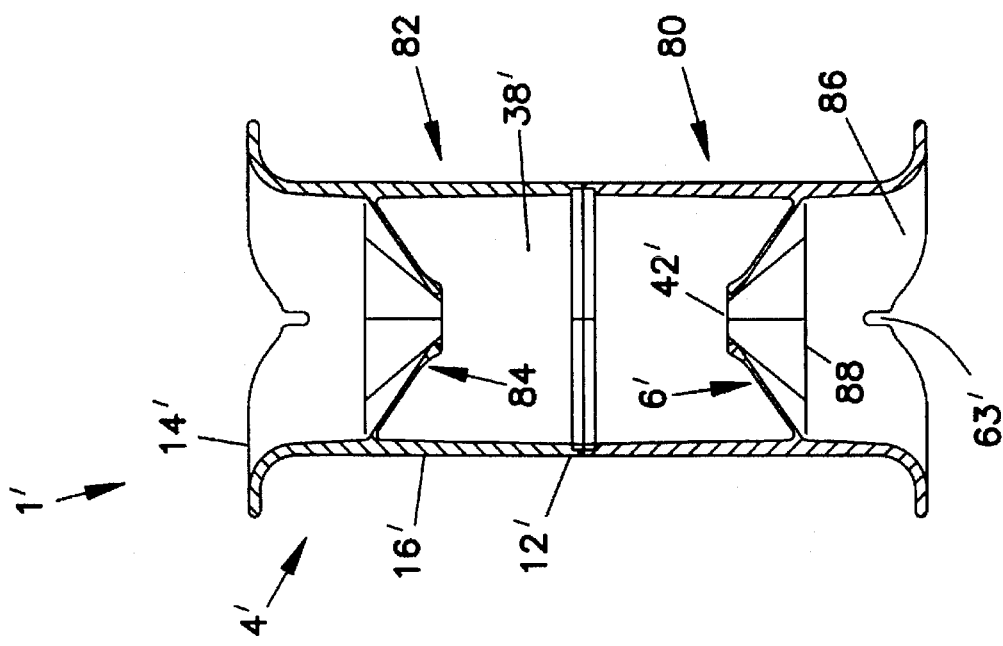
FIG. 14 is a cross-sectional view of a second preferred embodiment of the apparatus of the present invention.
Figure 21:
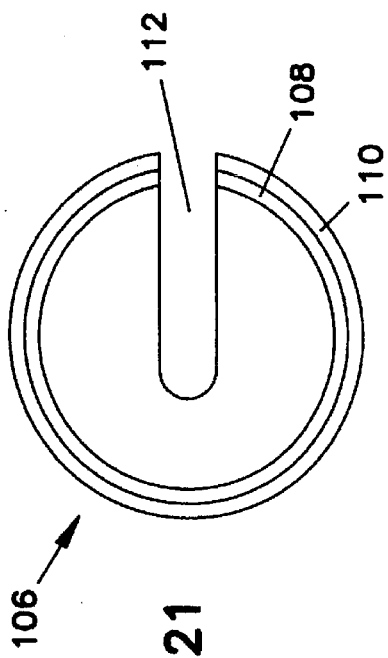
FIG. 21 is a plan view of the adaptor of FIG. 20.
Figure 22:
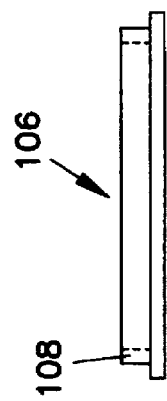
FIG. 22 is a side view of the adaptor of FIG. 20.

FIGS. 14–15 depict another preferred embodiment of the present invention. In this embodiment, apparatus 1' is preferably composed of two essentially, more preferably exactly, identical halves, i.e., a proximal half 80 and a distal half 82. Generally, the distal half 82 functions as a cap member 4' having a peripheral wall 16' defining an interior space. Further, the distal half has a basin-shaped member 84 having a self-closing passageway connected to the peripheral wall on the inside surface thereof, intermediate the distal end 14' and the proximal end 12' of the distal half 82. Similarly, the proximal half 80 has a peripheral wall defining an interior space and has a basin-shaped member 6' connected to the peripheral wall on the interior surface thereof intermediate the distal end and the proximal end of the proximal half. The proximal portion 86 of the proximal half 80 preferably has a wall that diverges slightly for spreading the pressure evenly on the skin of a patient. The distal end 14' of the distal member 82 preferably has a wall that diverges slightly to facilitate the introduction of a needle-removal device thereinto. The two halves can be secured together, for example, by securing arrangements such as an adhesive, adhesive tape, a clamp, a matingly engageable arrangement similar to arrangements 90 shown in FIG. 16–17 below, and the like. After the two halves are secured together, the basin-shaped members of the two halves have their respective apical ends 42' extending toward each other. This configuration permits a medical needle to be drawn into a cavity 38' defined between the peripheral walls and the basin-shaped members 6' of the two halves by passing through the self-closing passageway defined by the basin-shaped member 6' of the proximal half 80.

The basin-shaped member 6' can have a dome-shaped configuration similar to that shown in FIGS. 8–10. An alternative is a generally conical-basin-shaped member having fingers 40' that are generally straight as those shown in FIGS. 14 and 15. The fingers are shaped like generally isosceles triangles with their bases 88 yieldably connected to the interior wall and apical ends 42' extending in a direction toward a cavity 38' defined between the basin-shaped member 6' and the walls of the two halves. Again, preferably, the tips of the fingers are slightly spaced apart to facilitate the introduction of a needle-removal device or the withdrawal of a medical needle therethrough into the cavity 38'. The diverging portion of the proximal half has notches 63' through which a medical tubing connected to the medical needle and/or portal can extend therethrough. This embodiment has the advantage that the two halves are identical and therefore can be molded with the same molding machine, thereby greatly reducing the tooling expense for manufacturing and simplifying the assembly of the apparatus.

Another preferred embodiment having corresponding halves 89A, 89B that are substantially similar is shown in FIGS. 16–19. The apparatus 1" (shown in FIGS. 16–17 with self-closing passageways absent for the sake of clarity) is substantially symmetrical along a plane extending between the distal end 14" and the proximal end 12" of the apparatus. Each half is generally half-tube-shaped and extends through the full length of the apparatus 1". The apparatus 1" has corresponding matingly engageable arrangements 90 for snap-fit fastening the corresponding halves to each other. The corresponding matingly engageable arrangements can comprise an arrowhead or a half arrowhead 92 on one half and a slot 94 for receiving the arrowhead or the half arrowhead 92 on the other half. As shown in FIG. 17, the half arrowhead of a first half extends in the direction of the other half. During assembly, the wedge-shaped part of the half arrowhead slides along the wall of the other half until it reaches the slot 94 and slides thereinto with a snap-fit to engage the other half. Preferably, each half has a half arrowhead and a slot on two separate longitudinal edges so that the two halves can be fastened together in a snap-fit fashion.

Proximate the distal end of each half are ridges 96 defining a groove 97 therebetween for receiving a cover member 98 having a rim 100. Similarly, each half has parallel ridges 102 defining a groove 104 for receiving a basin-shaped member 6" at a location intermediate the distal end and proximal end of the apparatus. Notches 63" are provided on the proximal portion 62" of the apparatus at the proximal end 12" thereof for a medical tubing connected to a medical needle to extend therethrough.

Referring to FIG. 18, the cover member 98 has a rim 100 that can rotationally fit in the groove 97 defined by the parallel ridges 96 on the distal end 14" of the apparatus, i.e. on the two corresponding halves. The cover member 98 preferably has a configuration that is generally similar to the upper portion of cap member 4 shown in FIGS. 4–7 and is generally disc-shaped. The arrangement of the passageway is the same as that of FIGS. 4–7. For example, the cover member has flaps 22" and lips 30" similar to those of FIGS. 4–7.

The basin-shaped member 6" is preferably one depicted in FIG. 19, which shows a member having a configuration substantially similar to that of FIGS. 8–10 of the first embodiment described hereinabove. For example, the basin-shaped member 6" has umbrella-section-shaped fingers 40" with elevated elements 47". One difference between the two basin-shaped members is that in the present embodiment, the basin-shaped member 6" does not have a skirt (shown as 50 in FIG. 10) but has a generally flat rim 36" that rotationally fits in the grooves 104 defined by the parallel ridges 102 of the two corresponding halves in a position intermediate the distal end 14" and the proximal end 12" of the apparatus.

During assembly, the cover member 98 and the basin-shaped member 6" are positioned such that their corresponding rims are disposed in the corresponding grooves of the first half. Then, the second half is pressed onto the first half so that the corresponding matingly engageable arrangements 90 snap-fit to fasten the two halves together, thereby rotationally confining the respective rims of cover member 98" and the basin-shaped member 6" in their corresponding grooves 97,102. A cavity (not shown in FIGS. 16–19) is formed between the cover member and the basin-shaped member for isolating a medical needle therein.

Although in the above-described embodiment, a cover member and a basin-shaped member are used to define a cavity in conjunction with the peripheral wall of the apparatus, an apparatus can be constructed such that identical members each defining a self-closing passageway can be disposed at or proximate the distal end and in a position intermediate the distal end and the proximal end. For example, two basin-shaped members as shown in FIG. 19 can be disposed in the grooves 97,102 of the structures shown in FIG. 16. An alternative is to dispose two members shown in FIG. 18 in the grooves of the structures shown in FIG. 16. In each case, the basin-shaped members and the members with flaps are disposed such that the apical ends of the two basin-shaped members, or the flaps of the two members containing flaps, face the cavity.

As previously described, when used on a patient with an implanted access device, the apparatus is pressed onto the skin above the portal of the implanted access device. Because implanted access devices of different sizes can be used for different medical purposes, a small implanted access device can sometimes be so small that the proximal end of the body of apparatus 1 is much larger than the portal of the implanted access device and not provide sufficient pressure on the implanted access device. In such a case, an adaptor can be disposed between the apparatus and the skin for adapting the apparatus for use on the small implanted access device. One preferred embodiment of an adaptor of the present invention is shown in FIGS. 20–23. The adaptor 106 is generally disc-shaped having a generally annular ridge 108 proximate the rim 110 of the adaptor. The dimension of the ridge 108 can be such that the proximal end 8 of the apparatus 1 fits within the inside diameter of the ridge. Alternatively, if the implanted access device 68' is small enough, the annular ridge 108 can be disposed within the interior space of the proximal end of the body. The adaptor 106 has a slot 112 formed therein to allow the medical needle to extend therethrough. However, the slot is not of a dimension so large that the adaptor misses the portal of the implanted access device.

Figure 23:
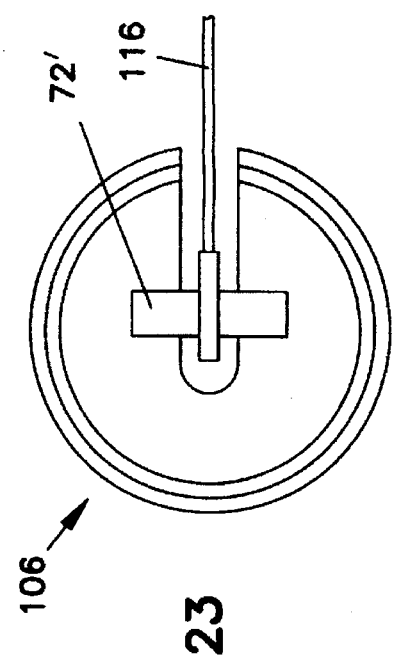
FIG. 23 is a top view showing the adaptor of FIG. 20 deployed underneath a butterfly needle.
Figure 20:
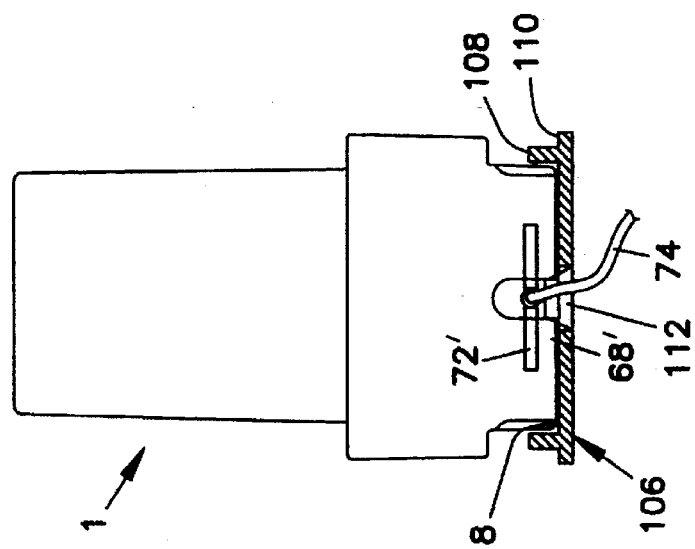
FIG. 20 is a partial cross-sectional view showing a preferred embodiment of an adaptor with an apparatus of FIG. 1 wherein details of the apparatus of FIG. 1 are shown schematically.

During use, the adaptor 106 can be slid along the surface of the skin for the medical needle to pass into the slot 112. For example, the adaptor can be slid under the butterfly wings 72' of a butterfly medical needle so that the butterfly wings and the medical tubing 74 are disposed in a position distal to the adaptor, as shown in FIG. 23. The body 2 of an apparatus 1 of the present invention, such as that shown in FIG. 1, can then be disposed on top of the adaptor 106 to hold the adaptor in place and to allow subsequent removal of the medical needle. FIG. 20 shows the cross-sectional view of the adaptor 106 taken at right angle to the slot 112 with an apparatus 1 (details of which has been omitted for clarity) of the present invention disposed on the adaptor. The adaptor 106 allows apparatus 1 to be more versatile. Apparatus 1 is useable with larger access devices without adaptor 106, and with small access devices with adaptor 106.

Figure 25:
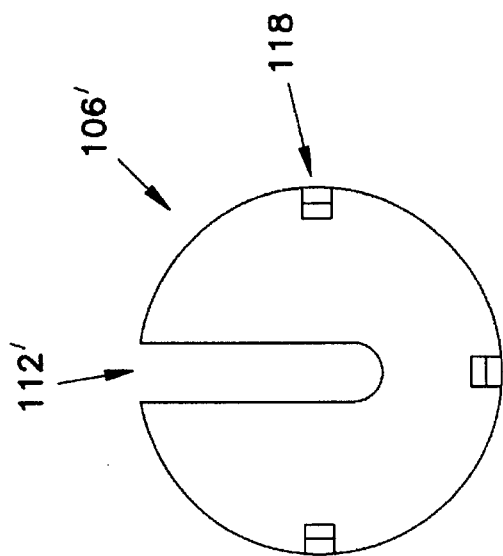
FIG. 25 is a plan view of the adaptor of FIG. 24.
Figure 26:
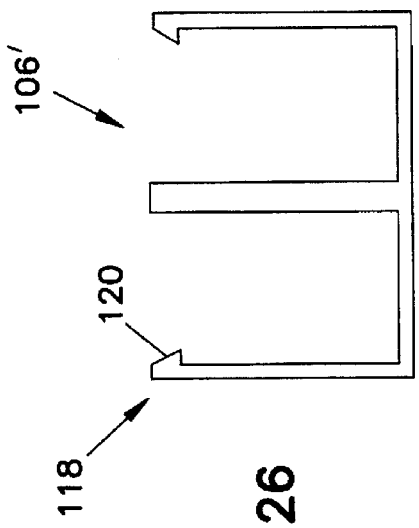
FIG. 26 is a side view of the adaptor of FIG. 24.
Figure 24:
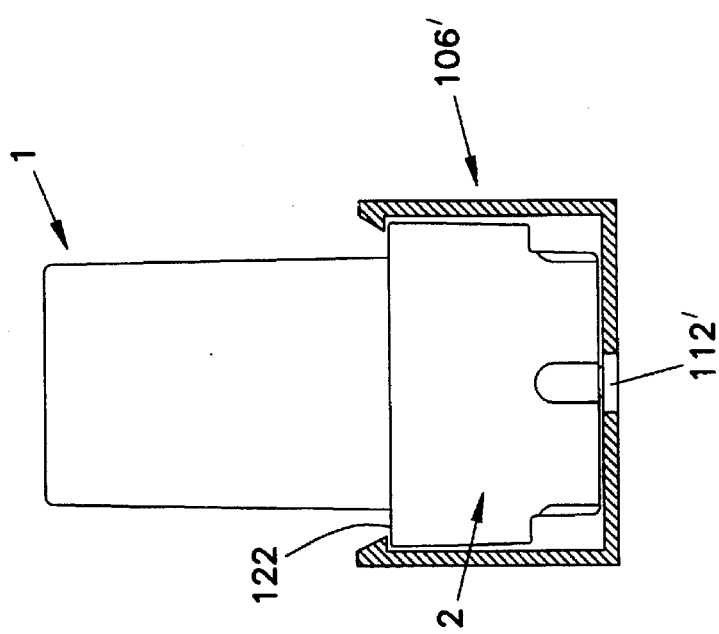
FIG. 24 is a partial cross-sectional view showing a second preferred embodiment of an adaptor of the present invention deployed with an apparatus of FIG. 1, wherein details of the apparatus of FIG. 1 and the needle are not shown for clarity.

Another alternative of an embodiment of an adaptor 106' is shown in FIGS. 24–26. In this embodiment, the adaptor 106' has a slot 112' as that in FIGS. 20–23. In addition, the adaptor 106' has peripheral gripping arrangements 118 such as wedge-shaped members 120 for securing the adaptor 106' to the body so that the apparatus 1, including the adaptor, can be deployed as a unit on the skin of a patient. The wedge-shaped members 120 of the adaptor extend distally and slide along the exterior surface of the body 2 and snap-fit over a distal edge 122 of the body 2. FIG. 24 shows the cross-sectional view of the adaptor 106' taken at a right angle to the slot 112' with an apparatus 1 (details of which has been omitted for clarity) of the present invention disposed on the adaptor.

The apparatus of the present invention can be made from plastic materials, preferably thermoplastics such as polystyrene, polycarbonate, polyacrylate, polypropylene, and the like. More preferably, the thermoplastic is a transparent material, such as polyacrylate, polycarbonate, polystyrene, and the like.

The present invention has been described in the foregoing specification. The embodiments are presented for illustrative purpose and are not to be interpreted as unduly limiting the scope of the invention. It is to be understood that modifications and alterations of the invention, especially in size and shape, will be apparent to those skilled in the art without departing from the spirit and scope of the invention. For example, the opening in the cap member can be guarded by a self-closing yieldable partition member that resembles any of the structures shown in FIGS. 8, 14, 18, and 19 and alternatives that provide a self-closing passage. For example, a flat flap or flaps (or fingers) extending perpendicular to the longitudinal axis of the device may be used. Similarly, the lower self-closing passageway intermediate the cap member and the proximal end of the apparatus can be any of these structures. Although the apparatus of the present invention is well-suited for removing butterfly needles, it is envisioned that the apparatus can be used for removing various types of medical needles from a substrate, such as the skin of a patient, a gauze, or the top of a table.

What is claimed is:

1. An apparatus for safely handling a needle while removing the needle from a substrate, the apparatus having a distal end and a proximal end and comprising:

a body defining an interior thereof;

a cap member defining an interior and an opening therein to access the interior of the cap member, the cap member being connected to and being distal to the body; and a basin-shaped member having a rim connected to the body, the basin-shaped member defining a self-closing passageway and the rim being disposed within the interior of the body intermediate the cap member and the proximal end of the apparatus, the basin-shaped member having an apical end facing the distal end of the apparatus, the basin-shaped member having a plurality of non-overlapping, side by side flexible fingers, the fingers each including a free end at the apical end of the basin-shaped member, the free ends defining an opening through the basin-shaped member when the fingers are in a relaxed state, the basin-shaped member defining a one way passageway for the needle, the fingers each extending from the rim of the basin-shaped member to the free end, the fingers defining a dome shape.

2. The apparatus according to claim 1, further comprising a resiliently flexible flap connected to the cap member at the opening.

3. The apparatus according to claim 1, further comprising two generally rectangular, resiliently flexible flaps extending obliquely at the opening toward each other from the cap member and toward the interior of the cap member, each flap terminating at a free edge, the free edges of the flaps being parallel and proximate to each other.

4. The apparatus according to claim 3, wherein the free edges of the flaps are offset from each other along a plane extending through the distal end and the proximal end.

5. The apparatus according to claim 3, wherein each flap has side edges which in cooperation with the free edge define the flap, and further comprising lips proximate the side edges extending from the cap member and oriented generally perpendicularly to the free edge of a flap.

6. The apparatus according to claim 1, wherein the basin-shaped member comprises an odd number of fingers forming a normally closed, yieldable partition.

7. The apparatus according to claim 1, wherein each finger includes an elevated element proximate only the free end, the elevated element having a longitudinal dimension proximate the free end facing toward a longitudinal axis of the apparatus.

8. The apparatus according to claim 1, wherein the cap member is rotatably connected to the body, the cap member being rotatable upon an axis extending through said distal end and the proximal end.

9. The apparatus according to claim 1, wherein the cap member and the body have a corresponding matingly engageable snap arrangement for snap-fit fastening the cap member to the body.

10. The apparatus according to claim 9, wherein the rim of the basin-shaped member is disposed and rotatably held between the cap member and the body.

11. The apparatus according to claim 1, wherein the rim of the basin-shaped member is disposed and rotatably held between the cap member and the body.

12. The apparatus according to claim 1, wherein a portion of the cap member and the body together define corresponding halves substantially symmetrical along a plane extending between the distal and the proximal end and wherein the apparatus has a corresponding matingly engageable snap arrangement for snap-fit fastening the corresponding halves to each other.

13. The apparatus according to claim 12, wherein the cap member comprises a cover member having a rim and including the opening, and wherein the corresponding halves of the cap member engage the rim of the cover member such that the cover member is held between the corresponding halves of the cap member proximate the distal end.

14. The apparatus according to claim 13, wherein a portion of the cap member and a portion of the body are integrally joined to form two corresponding integral halves each including a portion of the cap member and a portion of the body.

15. The apparatus according to claim 14, wherein the corresponding halves of the body engage the rim of the basin-shaped member such that the basin-shaped member is held between the corresponding halves of the body.

16. The apparatus according to claim 1 further comprising an adaptor disposed between the body and the substrate for adapting the use of the apparatus on an implanted vessel-access device, the adaptor having a generally planar portion defining a slot therein for the needle to extend therethrough so that the needle can be removed, a ridge extending from the generally planar portion positioned to engage the body, the generally planar portion reducing the size of an access opening to the apparatus defined by the body.

17. The apparatus according claim 16, wherein the adaptor includes a peripheral gripping arrangement for securing to the body so that the apparatus can be deployed as a unit.

18. An apparatus for safely handling a needle while removing the needle from a substrate, the apparatus having a distal end and a proximal end and comprising:
 a body defining an interior thereof;
 a cap member defining an interior and an opening therein to access the interior of the cap member, the cap member being connected to and being distal to the body;
 two flaps flexibly connected to the cap member to define at least a portion of the opening, the flaps extending obliquely toward each other and toward the interior of the cap member, each flap terminating at a free edge, the free edges of the flaps being parallel and proximate to each other; and
 a lower yieldable partition member connected to the body, the yieldable partition member defining a self-closing passageway, the self-closing passageway being disposed within the interior of the body intermediate the distal end and the proximal end of the apparatus.

19. The apparatus according to claim 18, wherein the free edges of the flaps are offset from each other in the direction toward the proximal end of the apparatus.

20. The apparatus according to claim 18, wherein the lower yieldable partition is basin-shaped.

21. An apparatus for safely handling a needle while removing the needle from a substrate, the apparatus having a distal end and a proximal end and comprising:
 a body defining an interior thereof;
 a cap member defining an interior and an opening therein to access the interior of the cap member, the cap member being connected to and distal to the body; and
 a lower yieldable partition member having a rim, the yieldable partition member defining a self-closing passageway and being disposed within the interior of the body intermediate the cap member and the proximal end of the apparatus;
 wherein the cap member and the body have a corresponding matingly engageable snap arrangement for snap-fit fastening the cap member to the body, wherein the rim of the yieldable partition member is disposed and rotatably held between the cap member and the body, wherein the cap member is rotatably moveable relative to the body.

22. The apparatus according to claim 21, wherein the lower yieldable partition is basin-shaped.

23. The apparatus of claim 21, wherein the body includes a generally cylindrical wall section, the generally cylindrical wall section including a plurality of wedge-shaped snap members disposed on an inner surface, and wherein the cap member includes a lower end and an outwardly extending annular lip at the lower end positioned to engage the snap members of the body, the lower end and the annular lip defining a plurality slits extending in a longitudinal direction of the apparatus.

24. An apparatus for safely handling a needle while removing the needle from a substrate, the apparatus having a distal end and a proximal end and comprising:
 a body defining an interior thereof;
 a cap member defining an interior and an opening therein to access the interior of the cap member, the cap member being connected to and distal to the body;
 a lower yieldable partition member connected to the body, the yieldable partition member defining a self-closing passageway; and
 an adaptor disposed between the body and the substrate for adapting the use of the apparatus on an implanted access device, the adaptor having a generally planar portion defining a slot therein for the needle to extend therethrough so that the needle can be removed from the substrate, a ridge extending from the generally planar portion positioned to engage the body, the generally planar portion reducing the size of an access opening to the apparatus defined by the body.

25. The apparatus according to claim 24, wherein the lower yieldable partition is basin-shaped.

26. An apparatus for safely handling a needle while removing the needle from a substrate, the apparatus comprising:
 a body construction defining an accessible interior for containing the needle, the body construction including spaced apart distal and proximal yieldable partition members each defining an opening and a self-closing passageway to each allow access to the interior of the body construction, the distal yieldable partition member including at least one resilient flap, the proximal yieldable partition member including a plurality of non-overlapping, side by side flexible fingers.

27. The apparatus of claim 26, wherein each yieldable partition member has an apical end facing each other.

28. A method for making an apparatus for safely handling a needle while removing the needle from a substrate, the apparatus having a distal end and a proximal end, the method comprising:

providing a body defining an interior thereof, a cap member defining an interior thereof and defining an opening therein, and a basin-shaped member, the basin-shaped member defining a self-closing passageway and having an apical end, wherein the cap member and the body each has a corresponding matingly engageable snap arrangement for snap-fit fastening the cap member to the body, wherein the cap member has a proximal end for contacting the basin-shaped member;

positioning the apical end of the basin-shaped member within the interior of the cap member wherein the cap member is positioned with the proximal end facing upward, wherein the apical end of the basin-shaped member is positioned within the interior of the cap member, and the basin-shaped member remains in contact with the proximal end of the cap member due to the effect of gravity; and snap-fit fastening the cap member and the body by engaging the corresponding matingly engageable snap arrangements of the cap member and the body, thereby confining the basin-shaped member in a position intermediate the proximal end and distal end of the apparatus, the cap member, the basin-shaped member, and the body all freely rotatable relative to one another.

29. An apparatus for safely handling a needle while removing the needle from a substrate, the apparatus having a distal end and a proximal end and comprising:

a body defining an interior thereof;

a cap member defining an interior and an opening therein to access the interior of the cap member, the cap member being connected to and being distal to the body;

a basin-shaped member having a rim connected to the body, the basin-shaped member defining a self-closing passageway and the rim being disposed within the interior of the body intermediate the cap member and the proximal end of the apparatus, the basin-shaped member having an apical end facing the distal end of the apparatus, the basin-shaped member having a plurality of non-overlapping, side by side flexible fingers, the fingers each including a free end at the apical end of the basin-shaped member, the free ends defining an opening through the basin-shaped member when the fingers are in a relaxed state, the basin-shaped member defining a one way passageway for the needle; and a resiliently flexible flap connected to the cap member at the opening.

30. The apparatus according to claim 29, further comprising a second resiliently flexible flap connected to the cap member at the opening, the two flaps being generally rectangular, the two flaps extending obliquely at the opening toward each other from the cap member and toward the interior of the cap member, each flap terminating at a free edge, the free edges of the flaps being parallel and proximate to each other.

31. The apparatus according to claim 30, wherein the free edges of the flaps are offset from each other along a plane extending through the distal end and the proximal end.

32. The apparatus according to claim 30, wherein each flap has side edges which in cooperation with the free edge define the flap, and further comprising lips proximate the side edges extending from the cap member and oriented generally perpendicularly to the free edge of a flap.

33. An apparatus for safely handling a needle while removing the needle from a substrate, the apparatus having a distal end and a proximal end and comprising:

a body defining an interior thereof;

a cap member defining an interior and an opening therein to access the interior of the cap member, the cap member being connected to and being distal to the body; and a basin-shaped member having a rim connected to the body, the basin-shaped member defining a self-closing passageway and the rim being disposed within the interior of the body intermediate the cap member and the proximal end of the apparatus, the basin-shaped member having an apical end facing the distal end of the apparatus, the basin-shaped member having a plurality of non-overlapping, side by side flexible fingers, the fingers each including a free end at the apical end of the basin-shaped member, the free ends defining an opening through the basin-shaped member when the fingers are in a relaxed state, the basin-shaped member defining a one way passageway for the needle, wherein the basin-shaped member includes an odd number of fingers forming a normally closed, yieldable partition.

34. An apparatus for safely handling a needle while removing the needle from a substrate, the apparatus having a distal end and a proximal end and comprising:

a body defining an interior thereof;

a cap member defining an interior and an opening therein to access the interior of the cap member, the cap member being connected to and being distal to the body;

a basin-shaped member having a rim connected to the body, the basin-shaped member defining a self-closing passageway and the rim being disposed within the interior of the body intermediate the cap member and the proximal end of the apparatus, the basin-shaped member having an apical end facing the distal end of the apparatus, the basin-shaped member having a plurality of non-overlapping, side by side flexible fingers, the fingers each including a free end at the apical end of the basin-shaped member, the free ends defining an opening through the basin-shaped member when the fingers are in a relaxed state, the basin-shaped member defining a one way passageway for the needle; and a needle grasping tool insertable through the opening of the cap member, through the interior of the body and through the basin-shaped member in a direction from the cap member toward the basin-shaped member, the needle grasping tool retractable past the basin-shaped member to permit release of the needle in the interior of the body between the basin-shaped member and the cap member, the needle grasping tool selectively operable to grasp and release the needle.

35. The apparatus of claim 34, further comprising a yieldable partition member mounted to the cap member and defining a self-closing passageway at the opening of the cap member.

36. The apparatus of claim 35, wherein the yieldable partition member includes two flaps extending from the cap member at the opening of the cap member, the two flaps extending obliquely toward each other and toward the interior of the cap member.

\* \* \* \* \*